United States Patent
Barth et al.

(10) Patent No.: US 6,802,882 B2
(45) Date of Patent: Oct. 12, 2004

(54) NITRIFICATION INHIBITORS, AND THE USE OF POLYACIDS WHICH CONTAIN A NITRIFICATION INHIBITOR FOR THE TREATMENT OF INORGANIC FERTILIZERS

(75) Inventors: Thomas Barth, Ludwigshafen (DE); Norbert Rieber, Mannheim (DE); Randall Evan Gold, Apex, NC (US); Jürgen Dressel, Neuhofen (DE); Klaus Erhardt, Leimen (DE); Klaus Horchler von Locquengh, Limburgerhof (DE); Edgar Leibold, Frankenthal (DE); Stefan Rittinger, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 54 days.

(21) Appl. No.: 10/265,499

(22) Filed: Oct. 7, 2002

(65) Prior Publication Data

US 2003/0145641 A1 Aug. 7, 2003

Related U.S. Application Data

(62) Division of application No. 09/680,195, filed on Oct. 6, 2000, now Pat. No. 6,488,734, which is a division of application No. 09/230,841, filed as application No. PCT/EP97/04278 on Aug. 6, 1997, now Pat. No. 6,139,596.

(30) Foreign Application Priority Data

Aug. 6, 1996 (DE) .......................................... 196 31 764

(51) Int. Cl.⁷ ................................................ C05G 5/00
(52) U.S. Cl. ...................................................... 71/64.1
(58) Field of Search ............................ 71/64.1, 31, 28, 71/34, 58, 63, 902

(56) References Cited

U.S. PATENT DOCUMENTS

| 3,635,690 A | 1/1972 | Griffith | 71/1 |
| 4,522,642 A | 6/1985 | Arndt et al. | 71/11 |
| 4,523,940 A | 6/1985 | Arndt et al. | 71/11 |
| 4,975,107 A | 12/1990 | Arndt et al. | 71/11 |
| 5,174,806 A | 12/1992 | Masuda | 71/29 |
| 5,482,529 A | 1/1996 | Ahlnas et al. | 71/33 |

FOREIGN PATENT DOCUMENTS

| AU | 5301279 | 5/1981 |
| CA | 4405393 | 8/1995 |
| CA | 2208529 | 7/1996 |
| DE | 222471 | 5/1985 |
| DE | 260486 | 9/1988 |
| DE | 273829 | 11/1989 |
| DE | 4128828 | 3/1993 |
| DE | 4405393 | 8/1995 |
| DE | 4446194 | 6/1996 |
| EP | 166420 | 1/1986 |
| WO | 89/09200 | 10/1989 |

OTHER PUBLICATIONS

Chem. Abst., 112 (13), AN117849f, no date.
Chem. Abst., 113 (17), AN151358a, no date.
Chem. Abst., 118 (15), AN146794p, no date.

Primary Examiner—Wayne A. Langel
(74) Attorney, Agent, or Firm—Keil & Weinkauf

(57) ABSTRACT

The use of inorganic or organic polyacids for the treatment of inorganic fertilizers, in particular the use of the polyacids as a mixture with at least one nitrification inhibitor for the treatment of inorganic fertilizers; the use of selected pyrazole derivatives as nitrification inhibitor in inorganic fertilizers and also as stabilizers of liquid manure or liquid fertilizer formulations, as well as the corresponding treated inorganic fertilizers per se; and novel pyrazole derivatives which can be used as nitrification inhibitors in inorganic fertilizers and also as stabilizers of liquid manure or liquid fertilizer formulations are described.

2 Claims, No Drawings

NITRIFICATION INHIBITORS, AND THE USE OF POLYACIDS WHICH CONTAIN A NITRIFICATION INHIBITOR FOR THE TREATMENT OF INORGANIC FERTILIZERS

This is a divisional application of U.S. Ser. No. 09/680,195, filed Oct. 6, 2000, U.S. Pat. No. 6,488,734, which is a divisional application of U.S. Ser. No. 09/230,841, filed Sep. 24, 1999, U.S. Pat. No. 6,139,596, which in turn is a PCT National Stage application of PCT/EP 97/04278, filed Aug. 6, 1997.

The invention relates to the use of inorganic or organic polyacids for the treatment of inorganic fertilizers.

In particular, the invention relates to the use of polyacids as a mixture with at least one nitrification inhibitor for the treatment of inorganic fertilizers, the use of selected pyrazole derivatives as nitrification inhibitor in inorganic fertilizers, and as stabilizers of liquid manure or liquid fertilizer formulations, and the corresponding treated inorganic fertilizers per se. Moreover, the present invention relates to pyrazole derivatives which can be used as nitrification inhibitors in inorganic fertilizers, and as stabilizers of liquid manure or liquid fertilizer formulations.

In order to make available to plants in agriculture the nitrogen needed by them, ammonium compounds are mainly employed as fertilizers.

Ammonium compounds are converted microbially to nitrates in the soil in a relatively short time (nitrification). Nitrates, however, can be washed out of the soil. The portion washed out is in this case no longer available for plant nutrition, so that for this reason rapid nitrification is undesirable. For better utilization of the fertilizer, nitrification inhibitors are therefore added to the fertilizer. A known group of nitrification inhibitors are pyrazole compounds.

A problem in the use of pyrazole compounds as nitrification inhibitors is their high volatility. During the storage of fertilizer preparations containing pyrazole compounds, a continuous loss of active compound occurs due to evaporation. The pyrazole compounds must therefore be formulated in a nonvolatile form by means of suitable measures.

To fix the pyrazole compounds, these were converted, for example, into transition metal complexes such as zinc complexes. This is described, for example, in U.S. Pat. No. 4,522,642. The volatility of the active compounds can thus be reduced. For environmental protection reasons, the widespread application of zinc, copper or manganese to the soil is, however, undesirable. Complexes of alkali metals or alkaline earth metals which are environmentally tolerable, are not adequately stable, however, and hydrolyze in the aqueous environment.

It has furthermore been attempted by neutralization of the pyrazole compounds with mineral acids, such as phosphoric acid or hydrochloric acid, to decrease their volatility. DE-A-4 128 828 describes the use of nitrates and phosphates of 3-methylpyrazole for the coating of fertilizers. U.S. Pat. No. 3,635,690 also describes the stabilization of pyrazole derivatives by mineral acids, such as hydrochloric acid, sulfuric acid, nitric acid and phosphoric acid. These acidic salts of the pyrazole compounds, however, are increasingly susceptible to hydrolysis and for this reason cannot be employed for all applications.

DE-A-4 128 828 further describes the sealing of the coated fertilizer with wax or oil. In the case of hygroscopic active compound salts, however, this process does not lead to a satisfactory resistance to hydrolysis.

Formulations of pyrazoles with polymeric auxiliaries have furthermore been employed. Thus DE 260 486 describes formulations of pyrazoles in urea-formaldehyde condensates. The incorporation of the active compounds into the polymer matrix, however, suppresses the mobility of the active compounds in the soil. In this application form, therefore, the finely divided formulation and fertilizer must be thoroughly mixed with the soil to be fertilized. Otherwise the nitrification inhibitor remains on the surface of the earth with the polymer matrix. The need to mix formulation, fertilizer and soil, however, is laborious.

It is an object of the present invention to provide inorganic fertilizers which contain a nitrification inhibitor whose content does not significantly change during storage and application of the fertilizer, and which remains in the ground after application of the fertilizer and can display its action there. Furthermore, new nitrification inhibitors shall be provided.

We have found that this object is achieved by use of inorganic or organic polyacids for the treatment of inorganic fertilizers. In this case, the treated inorganic fertilizer contains a nitrification inhibitor which is present in the inorganic fertilizer or on its surface. The nitrification inhibitor can furthermore also be employed as a mixture with the polyacid and then passes into this during the treatment of the inorganic fertilizer employed according to the invention, preferably onto the surface thereof.

The use of inorganic or organic polyacids for the treatment of inorganic fertilizers which contain nitrification inhibitors leads to an improved fixation of the nitrification inhibitors in the inorganic fertilizer. The volatility of the nitrification inhibitor is greatly reduced in this case, so that the storage stability of the treated inorganic fertilizer increases. Loss of nitrification inhibitor during a storage period or on application to the soil is avoided.

In addition, the treatment according to the invention and the treated inorganic fertilizer thus obtained have the advantage of ecological acceptability. They contain no toxic substances, such as, for example, zinc, copper or manganese, which in relatively large amounts very severely restrict environmental tolerability and can lead to soil contamination.

The treatment according to the invention can furthermore be carried out in a cost-efficient and ecologically tolerable manner. As a result of the treatment according to the invention, the amount of nitrification inhibitors in the inorganic fertilizer can be reduced because of the decreased volatility, which leads to decreased costs and to a better environmental tolerability of the fertilizers according to the invention. The object is furthermore achieved by the use of compounds of the general formula

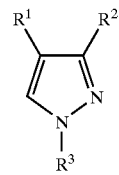

where the radical $R^1$ is a hydrogen atom, a halogen atom or a $C_{1-4}$-alkyl radical, the radical $R^2$ is a $C_{1-4}$-alkyl radical and the radical $R^3$ is H or a radical $-CH_2OH$, where if $R^3$ is H the salt of the compounds with phosphoric acid can also be employed, as nitrification inhibitors. Preferably the compound used is 3,4-dimethyl pyrazole, 4-chloro-3-methylpyrazole or a phosphoric acid addition salt thereof.

Polyacids

According to the invention, inorganic or organic polyacids are used for the treatment of the inorganic fertilizers.

In this case, all suitable inorganic or organic polyacids can be used which decrease the tendency of nitrification inhibitors to evaporate.

Inorganic polyacids which can be used according to the invention are isopolyacids or heteropolyacids, in particular polyphosphoric acids or polycyclic acids. The polyphosphoric acids, for example, have the general formula $H_{n+2}P_nO_{3n+1}$, n being an integer of at least 2, preferably at least 10.

Further inorganic polyacids which can be used are known to the person skilled in the art.

Suitable organic polyacids are those polymers which have a plurality of free carboxylic acid groups. These can be homo- or copolymers. Suitable monomers containing carboxyl groups or carboxylic acid groups are, in particular, monoethylenically unsaturated mono- or dicarboxylic acids having from 3 to 6 C atoms or their corresponding anhydrides, such as, for example, acrylic acid, methacrylic acid, ethylacrylic acid, allylacetic acid, crotonic acid, vinylacetic acid, maleic acid, itaconic acid, mesaconic acid, fumaric acid, citraconic acid, methylenemalonic acid, as well as their esters, such as, for example, monoalkyl maleates, and mixtures thereof. In the case of monoalkyl dicarboxylates, the number of C atoms specified relates to the dicarboxylic acid structure, the alkyl group in the ester radical, independently thereof, can have from 1 to 20 C atoms, in particular from 1 to 8 C atoms. Suitable appropriate monoethylenically unsaturated dicarboxylic anhydrides are maleic anhydride, itaconic anhydride, citraconic anhydride and mixtures thereof. Acrylic acid, methacrylic acid, maleic acid, itaconic acid and maleic anhydride are preferably employed. Acrylic acid is particularly preferably employed.

These monomers containing carboxyl groups or containing carboxylic acid groups can be homopolymerized or copolymerized with further vinylic monomers, such as, for example, $C_{1-8}$-, preferably $C_{1-4}$-alkylenes, in particular ethylene or propylene.

The organic polyacid particularly preferably used is polyacrylic acid or polymethacrylic acid.

The inorganic or organic polyacids can be employed as free acids or as partially neutralized ammonium, alkali metal or alkaline earth metal salts thereof. They are preferably employed as free acids.

Polyphosphoric acid and poly(meth)acrylic acid are particularly preferred.

The mean molecular weight of the organic polyacids is preferably from 10,000 to 500,000, particularly preferably from 10,000 to 100,000, in particular from 30,000 to 70,000.

Processes for the preparation of the polyacids are known to the person skilled in the art.

Nitrification Inhibitors

Any desired suitable nitrification inhibitors can be employed in the inorganic fertilizers according to the invention.

The polyacids used according to the invention are particularly advantageously employed for the treatment of inorganic fertilizers which contain these volatile nitrification inhibitors, in particular pyrazole compounds. "Pyrazole compounds" is understood as meaning all pyrazole compounds which have a nitrification-inhibiting action, such as are also described, for example, in the publications U.S. Pat. Nos. 3,635,690, 4,522,642 and DE-A-4 128 8-28 mentioned at the beginning in the discussion of the prior art, whose contents with respect to the pyrazole compounds described there are hereby included.

According to one embodiment, the pyrazole compounds used as nitrification inhibitors are those of the general formula below

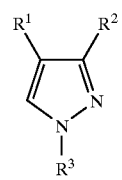

where the radicals $R^1$, $R^2$ and $R^3$ independently of one another are halogen atoms, nitro groups, hydrogen atoms or $C_{1-20}$-, preferably $C_{1-4}$-alkyl radicals, $C_{3-8}$-cycloalkyl radicals, $C_{5-20}$-aryl radicals or alkylaryl radicals, where the last-mentioned 4 radicals can be monosubstituted or trisubstituted by halogen atoms and/or hydroxyl groups.

The radical $R^1$ is preferably a hydrogen atom, a halogen atom or a $C_1$–$C_4$-alkyl radical, the radical $R^2$ is a $C_{1-4}$-alkyl radical and the radical $R^3$ is a hydrogen atom or a radical —$CH_2OH$.

According to a further embodiment of the invention, the radical $R^1$ in the above formula is a halogen atom or $C_{1-4}$-alkyl radical, the radical $R^2$ is a $C_{1-4}$-alkyl radical and the radical $R^3$ is a hydrogen atom or a radical —$CH_2CH_2COOH$ or —$CH_2CH(CH_3)COOH$.

The pyrazole compounds can be employed in the basic form, and also in the form of acid addition salts with inorganic mineral acids and organic acids. Examples of inorganic mineral acids are hydrochloric acid, phosphoric acid, sulfuric acid, preferably phosphoric acid. Examples of organic acids are formic acid, acetic acid, and also fatty acids. Examples of these salts are the hydrochlorides and phosphoric acid addition salts.

The pyrazole compounds can be employed on their own or in the form of mixtures.

Particularly preferred pyrazole compounds are 3,4-dimethylpyrazole, 4-chloro-3-methylpyrazole, N-hydroxymethyl-3,4-dimethylpyrazole, N-hydroxymethyl-4-chloro-3-methylpyrazole as well as the phosphoric acid addition salts of 3,4-dimethylpyrazole and 4-chloro-3-methylpyrazole as well as the hydrochloride of 3,4-dimethyl-pyrazole.

By use of the acid addition salts of the pyrazole compounds, the volatility of the compounds can be further reduced. Thus acid addition salts of the pyrazole compounds are advantageously employed in combination with the treatment according to the invention.

Halogen atoms employed in the above compounds are fluorine, chlorine, bromine or iodine, preferably fluorine, chlorine or bromine.

The preparation of the pyrazole compounds used according to the invention is known. It is described, for example, in EP-A-0 474 037, DE-A 3 840 342 and EP-A-0 467 707. For preparation of the N-hydroxymethylpyrazoles, the corresponding pyrazoles are reacted with formalin solution in methanol. Excess solvent is then evaporated, the compounds being obtained as solids. For the preparation of 3,4-dimethylpyrazole reference is made to Noyce et al., Jour. of Org. Chem. 20, 1955, 1681 to 1682.

The acid addition salts of the pyrazole compounds are obtained by reaction of the pyrazoles with an equivalent of appropriate acid. The preparation of the hydrochloride of 4-chloro-3-methyl-pyrazol is described in Hüttel et al., Liebigs Ann. Chem. 1956, 598, 186, 194.

Treated Inorganic Fertilizers

According to the invention, inorganic fertilizers are employed. These are ammonium- or urea-containing fertilizers. Examples of ammonium-containing fertilizers of this type are NPK fertilizers, calcium ammonium nitrate, ammonium sulfate nitrate, ammonium sulfate or ammonium phosphate.

The treated inorganic fertilizer according to the invention can be present in powder form or in granule form.

The inorganic fertilizers treated according to the invention contains at least one nitrification inhibitor and is treated with at least one inorganic or organic polyacid. In this case, the inorganic fertilizer can be present as a mixture with the nitrification inhibitor. The nitrification inhibitor can also be present on the surface of the inorganic fertilizer and can then be treated with the polyacid according to the invention. Preferably, the nitrification inhibitor can be applied to the inorganic fertilizer as a mixture with the polyacid to be used according to the invention.

Preferably, the inorganic fertilizer contains as nitrification inhibitor a pyrazole compound or an acid salt thereof. Preferably, the inorganic fertilizer is treated with poly(meth) acrylic acid or polyphosphoric acid.

Preferably, the inorganic fertilizer contains from 0.01 to 1.5% by weight of nitrification inhibitor and from 0.01 to 1.5% by weight of polyacid, based on the treated inorganic fertilizer.

The present invention furthermore relates to inorganic fertilizers comprising a compound of the above general formula, as is defined above, and a treated inorganic fertilizer comprising the abovementioned inorganic fertilizer, which is treated with at least one inorganic or organic polyacid or a mixture of at least one nitrification inhibitor and at least one inorganic or organic polyacid.

Preparation of the Treated Inorganic Fertilizers

The treated inorganic fertilizers according to the invention are prepared by treating the inorganic fertilizer with the polyacid. Preferably, they are prepared by treating the surface of the inorganic fertilizer with the polyacid.

In this case, the nitrification inhibitor can be present as a mixture with the inorganic fertilizer or can have been applied to the inorganic fertilizer before the polyacid. According to one embodiment of the invention, the inorganic fertilizer is treated with polyacid and nitrification inhibitor as a mixture.

In this case, the inorganic fertilizers are treated, e.g. impregnated or sprayed, with the polyacid, the nitrification inhibitor or mixture thereof by spraying them with a liquid preparation, e.g. a solution or suspension of the polyacid, of the nitrification inhibitor or of the mixture and, if desired, drying again. An appropriate process is described, for example in DE-A-4 128 828.

Preferably, nitrification inhibitor and polyacid are applied, e.g. sprayed, onto the inorganic fertilizer in the form of a liquid preparation, e.g. of a solution or suspension of the polyacid, and, if desired, then dried.

In this case, a mixture is preferably employed of from 30 to 98% by weight of at least one polyacid and from 2 to 70% by weight of at least one nitrification inhibitor in a liquid medium, preferably water. The nitrification inhibitor can in this case again be present as an acid addition salt.

The invention also relates to the use of compounds of the general formula

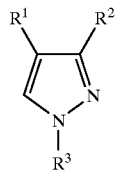

where
the radical $R^1$ is a hydrogen atom, a halogen atom or a $C_{1-4}$-alkyl radical,
the radical $R^2$ is a $C_{1-4}$-alkyl radical and the radical $R^3$ is H or a radical —$CH_2OH$, where if $R^3$ is H, the salt of the compounds with phosphoric acid can also be employed, as nitrification inhibitors.

Halogen atoms employed in the above compounds are fluorine, chlorine, bromine or iodine, preferably fluorine, chlorine or bromine.

Particularly preferred pyrazole compounds are 3,4-dimethylpyrazole, 4-chloro-3-methylpyrazole, N-hydroxymethyl-3,4-dimethylpyrazole, N-hydroxymethyl-4-chloro-3-methylpyrazole, as well as the phosphoric acid addition salts of 3,4-dimethylpyrazole and 4-chloro-3-methylpyrazole. N-Hydroxymethyl-3,4-dimethylpyrazole and N-hydroxymethyl-4-chloro-3-methylpyrazole are particularly preferred.

The present invention furthermore relates to a fertilization process, in which treated inorganic fertilizer, as defined in the context of the present application, is applied to the arable soil.

According to one embodiment of the present invention the nitrification inhibitors or inorganic fertilizers as described above are not used for treating soils which are used for corn, cotton, wheat, rice, barley and/or sugar-beet cultures or for treating the respective cultures.

The compounds of the above general formula can furthermore be used for the stabilization of liquid manure or liquid fertilizer formulations, such as, for example, ammonium nitrate-urea solutions or liquid ammonia.

The invention furthermore relates to N-hydroxymethyl-4-chloro-3-methylpyrazole, as well as the phosphoric acid addition salts of 3,4-dimethylpyrazole and 4-chloro-3-methylpyrazole per se, the hydrochloride of 3,4-dimethylpyrazole as well as mixtures of two or more thereof, which, of course, can also be used as nitrification inhibitors, preferably together with the polyacids used according to the invention.

The invention is further described below by means of examples.

EXAMPLES

Preparation of N-hydroxymethyl-3,4-dimethylpyrazole 96 g (1.0 mol) of 3,4-dimethylpyrazole in 50 ml of methanol were dissolved in 100 g (1.0 mol) of formalin solution (30%) at room temperature. Water and methanol were then evaporated. The title compound remained as a white solid (yield 95%).

Preparation of N-hydroxymethyl-4-chloro-3-methylpyrazole 116 g (1.0 mol) of 4-chloro-3-methylpyrazole in 50 ml of methanol were dissolved in 100 g (1.0 mol) of formalin solution (30%) at room temperature. Water and methanol were then evaporated. The title compound remained as a white solid (yield 95%).

Preparation of 3,4-dimethylpyrazolium dihydrogen Phosphate 96 g (1.0 mol) of 3,4-dimethylpyrazole were dissolved in 115 g (1.0 mol) of phosphoric acid (85%) at room temperature. The water contained in the phosphoric acid was evaporated. After a few hours, the title compound crystallized out from the oil initially present (yield 98%).

Preparation of 4-chloro-3-methylpyrazolium dihydrogen Phosphate 116 g (1.0 mol) of 4-chloro-3-methylpyrazole were dissolved in 115 g (1.0 mol) of phosphoric acid (85%) at room temperature. The water contained in the phosphoric acid was evaporated. After a few hours, the title compound crystallized out of the oil initially present (yield 98 %).

Preparation of the nitrification-inhibited Inorganic Fertilizers

The carrier fertilizer used was ammonium sulfate nitrate (ASN). 2 g of pyrazole were dissolved in a little water, and if desired (see Table I) the solution was mixed with a stoichiometric amount of phosphoric acid (1:1) and with from 1 to 10 g of polyacrylic acid or polyphosphoric acid. 2 g of the carrier fertilizer in the form of granules were prewarmed to approximately 50° C. and slowly sprayed onto a turntable with the mixture containing the pyrazole compound. To accelerate the drying, drying was carried out with hot air, either at the end of the spraying or after interruption of the spraying.

Investigation of the Storage Stability

The storage stability of the treated inorganic fertilizers was determined in a rapid test in which the nitrification-inhibited inorganic fertilizers were stored in a ventilated warming cabinet for 4 weeks at 30° C., from 40 to 50% relative atmospheric humidity and approximately 1.2 m/s air velocity. The concentration of nitrification inhibitor on the inorganic fertilizer was determined before and after storage and the loss of nitrification inhibitor determined in percent. Approximately 10 to 30 g of treated inorganic fertilizer were stored in each case. The concentration of pyrazole compound as nitrification inhibitor in this case was from 0.05% by weight to 0.2% by weight at the start of the investigation, based on the treated inorganic fertilizer. The losses obtained for different pyrazole compounds are shown in Table I below.

TABLE I

| Compound | Loss in percent |
| --- | --- |
| 3-Methylpyrazole* | 100% |
| 3,4-Dimethylpyrazole* | 100% |
| 4-Chloro-3-methylpyrazole* | 100% |
| 3-Methylpyrazole phosphate* | 55% |
| 3,4-Dimethylpyrazole phosphate* | 31% |
| 4-Chloro-3-methylpyrazole phosphate* | 92% |
| 3,4-Dimethylpyrazole + polyacrylic acid | 10% |
| 4-Chloro-3-methylpyrazole + polyacrylic acid | 5% |
| 3,4-Dimethylpyrazole phosphate + polyacrylic acid | 9% |
| 4-Chloro-3-methylpyrazole phosphate + polyacrylic acid | 12% |
| 3,4-Dimethylpyrazole + polyphosphoric acid (1:20) | 0% |
| 3,4-Dimethylpyrazole + polyphosphoric acid (1:1) | 12% |

* = Comparison experiments

It emerges from the results of Table I that the loss of pyrazole compound in the inorganic fertilizers treated according to the invention during storage is essentially lower than with the comparison substances. Coating with the polyacid according to the invention leads to a significantly reduced loss of nitrification inhibitor.

Demonstration of the Biological Effect of the Nitrification Inhibitors

Field Test

The biological effectiveness of 4-chloro-3-methylpyrazole (4 Cl-3MP) and 3,4-dimethylpyrazole (3,4-DMP) in comparison with DCD and the control was tested in multiple field tests in different environments by means of the features "nitrate content in the basis of the stem", "$NO_3$— and $NH_4$—N-content in the soil" as well as "grain produce".

The standard methods used in agricultural tests were applied to the laying-out, probing, harvesting and evaluation of the field tests.

The analysis of the plant and soil samples followed standard procedures. The remaining measures undertaken in the production, e.g. plant protection, were in accordance with good agricultural practice and were applied uniformly.

A biologically effective nitrification inhibitor is characterized preferably in that the soil to which it is applied shows lower amounts of $NO_3$—N and higher amounts of $NH_4$—N compared to a comparitive test (here: supporting fertilizer is ammonium sulfate salpeter without nitrification inhibitor) in a time period of up to 8 weeks after application (compare table 1).

As a consequence of this treatment the nitrate consumption of the plants is reduced (compare $NO_3$-content in the basis of the stem of rape plants, table 2) and the produce is enhanced (compare grain produce of winter wheat, tables 3a and 3b). Table 4 shows the description of the location of the field tests.

In the following table 1 the results are summarized. It is evident that all three nitrification inhibitors have good biological effectiveness compared to the control. 4 Cl-3 MP and 3,4-DMP show an effectiveness as good as or better than that of DCD, using reduced amounts of the active substance. Further examples relating to selected nitrification inhibitors are shown in table 5.

TABLE 1

Demonstration of the biological effect of different nitrification inhibitors
- field tests -
Ø NO3- and NH4-N-amounts in soil (n = 5)

| | weeks after application | | | | | | | |
| --- | --- | --- | --- | --- | --- | --- | --- | --- |
| | 2 | | 4 | | 6 | | 8 | |
| nitrification inhibitor | NO3-N kg/ha | NH4-N kg/ha | NO3-N kg/ha | NH4-N kg/ha | NO3-N kg/ha | NH4-N kg/ha | NO3-N kg/ha | NH4-N kg/ha |
| without | 82 | 97 | 75 | 49 | 61 | 50 | 43 | 20 |
| DCD | 47 | 87 | 44 | 68 | 35 | 82 | 29 | 39 |
| 4Cl-3MP | 61 | 115 | 50 | 79 | 39 | 76 | 28 | 40 |
| 3,4-DMP | 54 | 82 | 43 | 70 | 44 | 71 | 28 | 37 | locations: 1, 2, 3, 4 and 5: description see table 4

TABLE 2 demonstration of the biological effect of different nitrification inhibitors
- field tests -
Ø NO3 amount in the basis of the stem of rape plants (n = 5)

| | weeks after application | | | |
|---|---|---|---|---|
| | 2 | 4 | 6 | 8 |
| nitrification inhibitor | NO3 ppm | NO3 ppm | NO3 ppm | NO3 ppm |
| without | 8421 | 7255 | 5642 | 5194 |
| DCD | 8036 | 7022 | 4728 | 4274 |
| 4Cl-3MP | 8112 | 6629 | 4774 | 4276 |
| 3,4-DMP | 8105 | 6720 | 4899 | 4454 | locations: 1, 2, 3, 4 and 5: description see table 4

TABLE 3a demonstration of the biological effect of different nitrification inhibitors
- field tests -
grain produce of winter wheat

| nitrification inhibitor | grain produce dt/ha |
|---|---|
| without | 52.8 |
| DCD | 52.6 |
| 4Cl-3MP | 56.0 | location 4: description see table 4

TABLE 3b demonstration of the biological effect of different nitrification inhibitors
- field tests -
grain produce of winter wheat

| nitrification inhibitor | grain produce dt/ha |
|---|---|
| without | 95.4 |
| DCD | 94.3 |
| 3,4-DMP | 97.8 | location 2: description see table 4

TABLE 4 demonstration of the biological effect of different nitrification inhibitors
- field tests -
description of the location

| location | temperature per year ° C. | precipitation per year mm | type of soil * | arable soil number | pH-value | humus content % |
|---|---|---|---|---|---|---|
| 1 | 8.8 | 600 | L | 68 | 7.3 | 1.3 |
| 2 | 7.8 | 817 | tL | 43 | 6.6 | 1.4 |
| 3 | 10.1 | 740 | sL | 45 | 6.5 | 1.2 |

TABLE 4-continued demonstration of the biological effect of different nitrification inhibitors
- field tests -
description of the location

| location | temperature per year ° C. | precipitation per year mm | type of soil * | arable soil number | pH-value | humus content % |
|---|---|---|---|---|---|---|
| 4 | 9.9 | 550 | IS | 30 | 6.5 | 1.2 |
| 5 | 9.9 | 550 | L | 60 | 6.7 | 1.3 |

* L: loam
tL: lean clay
sL: sandy loam
IS: loamy sand

TABLE 5 nitrification inhibiting effect of different pyrazoles *

| compound | 1 | 2 | 4 | 6 | 8 |
|---|---|---|---|---|---|
| 3-methylpyrazole (3-MP) | 90 | 58 | 45 | 27 | 22 |
| 3,4-dimethylpyrazole (DMP) | 88 | 61 | 48 | 34 | 27 |
| 4Cl-3methylpyrazole (4Cl-3MP) | 88 | 66 | 48 | 32 | 21 |
| 4Cl-3methylpyrazolephosphate | 91 | 62 | 53 | 45 | 27 |
| N-hydroxy-4Cl-3MP | 87 | 58 | 45 | 30 | 15 |
| N-hydroxyl-3,4-DMP | 85 | 54 | 40 | 31 | 10 |

* % inhibition per applied amount of ammonium

We claim:
1. A method of stabilizing liquid manure or liquid fertilizer formulations comprising adding thereto at least one compound of the general formula

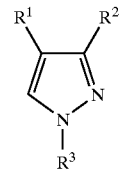

where $R^3$ is a radical —$CH_2OH$, the radical $R^1$ is a hydrogen atom, a halogen atom, or a $C_{1-4}$-alkyl radical, and the radical $R^2$ is a $C_{1-4}$-alkyl radical, with the exception of 1-hydroxymethyl-3-methylpyrazole, or
where the radical $R^3$ is H, the radical $R^1$ is a hydrogen atom or a $C_{1-4}$-alkyl radical and the radical $R^2$ is a $C_{1-4}$-alkyl radical, with the exception of 3-methylpyrazole and 3,4-dimethylpyrazole, or
a salt of the compound where the radical $R^3$ is H, the radical $R^1$ is a hydrogen atom, a halogen atom, or a $C_{1-4}$-alkyl radical, and the radical $R^2$ is a $C_{1-4}$-alkyl radical, with phosphoric acid, with the exception of 3-methylpyrazolephosphate and 4-bromo-3-methylpyrazolephosphate.

2. A method of stabilizing liquid manure or liquid fertilizer formulations as defined in claim 1, wherein the compound that is added thereto is chosen from the group consisting of N-hydroxymethyl-4-chloro-3-methylpyrazole, N-hydroxymethyl-3,4-dimethylpyrazole, phosphoric acid addition salt of 3,4-dimethylpyrazole, phosphoric acid addition salt of 4-chloro-3-methylpyrazole and hydrochloride of 3,4-dimethylpyrazole.

* * * * *